United States Patent [19]

Hudson

[11] 4,197,011
[45] Apr. 8, 1980

[54] DEFECT DETECTION AND PLOTTING SYSTEM

[75] Inventor: Kenneth C. Hudson, Philadelphia, Pa.

[73] Assignee: RCA Corporation, New York, N.Y.

[21] Appl. No.: 835,591

[22] Filed: Sep. 22, 1977

[51] Int. Cl.² .......................................... G01N 21/32
[52] U.S. Cl. ................................. 356/354; 250/550; 250/572; 356/237
[58] Field of Search ............... 356/109, 111, 237, 354; 250/550, 572

[56] References Cited

U.S. PATENT DOCUMENTS

| | | | |
|---|---|---|---|
| 3,748,047 | 7/1973 | McIlgard et al. | 250/572 X |
| 3,874,796 | 4/1975 | Chovan et al. | 250/550 X |
| 3,947,123 | 3/1976 | Carlson et al. | 350/162 SF X |
| 4,030,835 | 6/1977 | Firester et al. | 356/111 |
| 4,069,484 | 1/1978 | Firester et al. | 356/237 X |

*Primary Examiner*—F. L. Evans
*Assistant Examiner*—Matthew W. Koren
*Attorney, Agent, or Firm*—E. M. Whitacre; J. E. Roehling

[57] ABSTRACT

Defect detection apparatus provides a moving light beam which illuminates the surface of a rotating grooved disc with a light spot spanning a plurality of convolutions of the groove. The beam is translated to rapidly scan the grooved surfaces in a radial pattern. The structure of the groove convolutions, absent any defects, diffracts the incident beam producing a plurality of reflected beams. A first lens, provided in the path of the reflected beams, provides, in a focal plane thereof, a Fourier transformation of the light amplitude data of the respective reflected beams. A second lens, provided in the diffracted beam path downstream of the first lens, provides at the surface of a photodetector, an inverse Fourier transformation which is an image of the scanning spot. Blocking means, placed in the focal plane of the first lens intercept the reflected beams when defect-free groove regions are illuminated, to prevent the conversion of light energy to electric energy by the photodetector. When a defect exists in the illuminated region of the groove, portions of the reflected beams bypass the blocking means to produce in the photodetector electrical signals indicative of the presence of a defect. Writing apparatus, for mapping 1:1 polar plots of disc record defect locations on disc-shaped photosensitive paper supported on a turntable, accepts electrical signals representing defect occurrences after compensation for the presence of dust in the illuminated region. These signals activate a gate that permits passage of a recording beam of light to the surface of the turntable. Relative motion is established between the turntable and the recording beam in a manner causing markings resulting from gate activations to be located on the photosensitive paper with radial and circumferential positions corresponding to the locations of the defects appearing on the grooved disc.

5 Claims, 3 Drawing Figures

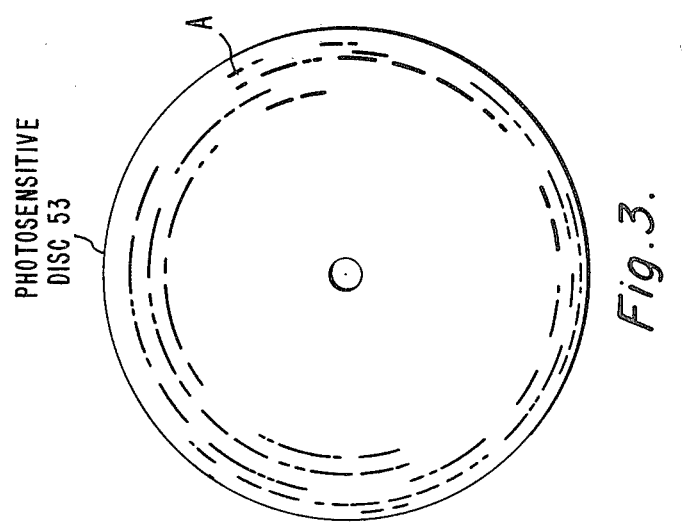
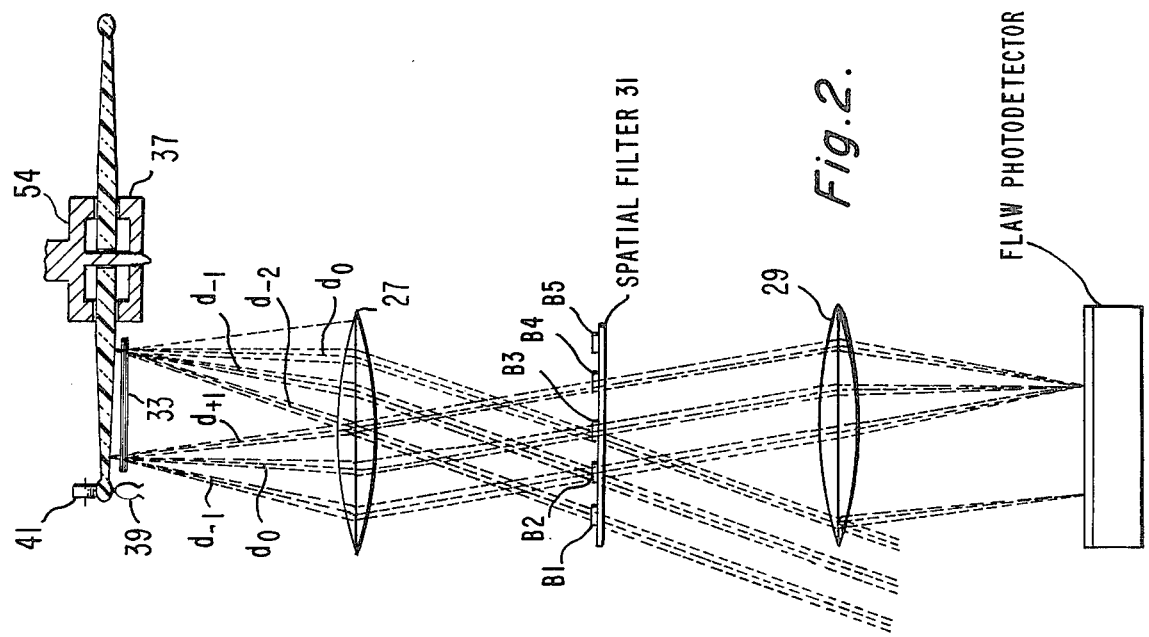

DEFECT DETECTION AND PLOTTING SYSTEM

The present invention relates generally to high speed optical defect detection and plotting systems and particularly to optical defect detection and plotting systems which may be employed to determine flaws in a regularly grooved high density information record, such as a video disc of the type described in U.S. Pat. No. 3,842,194, issued to Jon K. Clemens.

The defect detection and plotting principles of the present invention are applicable where faithful records of groove surface conditions are required speedily. An illustrative environment, where such application of the principles of the present invention is particularly advantageous, is the manufacture of video disc records. In the processes for manufacturing a video disc record, such as the type supra, formulation of a uniform spiral groove free of significant amounts of undesirable asperities is an important factor for obtaining high quality video signal recordings. Each stage of record manufacture can be a critical stage wherein undesirable build-up of asperities that affect the production of quality video records must be minimized.

In one illustrative process for producing high quality video disc records having spiral grooves, a spiral groove is made by mechanically cutting a trapezoidal cross-section groove in a copper-coated aluminum disc, and coating the grooved surface with an electron beam sensitive material. The coated disc is mounted on a turntable of an electron beam disc recorder in the path of a finely focused beam of electrons, that is turned on and off, exposing selected portions of the groove bottom as the disc is rotated and translated with respect to the impinging beam. Those portions of the groove struck by the electron beam are removed by subsequent development of the sensitive material. After exposure and development, the master disc has the relief pattern that is desired in the final records. Molds for making stampers for producing production line records are made from these masters. In the final stages of manufacturing a video disc, a vinyl substrate is formed with the desired relief pattern, using a stamper made from a mold; the substrate is coated with a metal by a vacuum sputtering process; the metal is coated with a styrene dielectric by a glow discharge process; and the styrene is coated with a layer of oil by an evaporation process.

During each of the above-described record manufacturing processes, various kinds of flaws can develop, which may affect the record groove quality, and which are difficult to detect in view of the fineness of the groove structure typically employed in video disc (e.g., 5555 groove convolutions per inch).

In accordance with one approach of detect detection in spirally grooved discs, explained in U.S. Pat. No. 4,069,484, to Firester, et al., an incident probing beam, focused at a point beyond the disc surface, illuminates the grooved surface with a light spot that spans a plurality of convolutions of the groove. Relative motion is established between the disc surface and the probing beam in a manner causing the illuminating spot to rapidly scan the grooved surfaces in a coarse spiral pattern. The structure of the illuminated groove convolutions, absent any defects, serves as a diffraction grating for diffracting the light into an undeviated zero diffraction order cone of light that converges at a first location in a plane spaced from the disc surface and into deviated higher diffraction order cones of light that converge at additional locations in said plane separated from the first location. A photodetector is positioned to be in registry with the first location and spaced from said additional locations. A blocking means is placed over a central region of the photodetector to normally intercept the zero diffraction order light, thereby preventing the conversion of light energy to electric energy by the photodetector when defect-free groove regions are illuminated. When a defect exists in the illuminated region of the groove, unblocked regions of the photodetector receive light and the photodetector produces electrical signals indicative of the presence of a defect.

In accordance with the principles of the present invention, the aforementioned light diffraction approach to defect detection of Firester, et al., is advantageously employed to provide accurate defect detection data in an extremely short time duration (e.g., of the order of 3 seconds). A probing light beam, focused at a point near the surface of a grooved disc, illuminates the grooved surface with a light spot having a half-intensity contour that spans a plurality of groove convolutions. The axis of the probing beam path lies in a non-parallel relationship, and at a chosen angle (e.g., 2°), with respect to the central axis of the disc. The incident beam axis is desirably positioned in a plane which is parallel to the disc's central axis and intersects the grooved surface along a tangent to a groove convolution at the point of incidence. The illuminated portion of the groove convolutions effectively forms a diffraction grating, which is uniform (in the absence of defects). The effect of the diffraction grating on light reflected from the grooved surface is to form diffraction order cones of light that converge at respective locations in a convergence plane spaced from the grooved surface.

In accordance with one aspect of the present invention, a first lens, which collects a large portion of the reflected light, provides a Fourier transformation in the focal plane of the first lens, of the light amplitude data in the convergence plane, while a second lens, provided in the diffracted light path downstream of the first lens, provides an inverse Fourier transformation, so that at the focal plane of the second lens an image of the scanning spot is reproduced on the surface of a photodetector. Blocking means are provided in the path of the reflected light to prevent the diffraction orders of light reflected from a defect-free groove structure and collected by the first lens from reaching the photodetector. By collecting a large portion of the reflected light, system sensitivity to defects is enhanced since large portions of the light scattered from groove defects will be preserved within the system.

When defects in the grooved surface are illuminated, the uniform diffraction grating effect is disturbed and some light, reflected from such a surface, will bypass the blocking means to reach the photosensitive surface of the photodetector, which produces an electrical signal output indicative of the defect presence.

Accurate positioning of the blocking means and the photodetector can insure that the diffracted light will not reach the photosensitive surface when defect-free regions of the disc surface are illuminated (the diffraction order components being intercepted by the blocking means), if one can safely assume that the disc surface in which the groove convolutions appear is otherwise flat and maintains a constant attitude relative to the incident beam. However, this assumption cannot be made in all instances. For example, a replicated disc is likely, due to effects of the replication processes, to exhibit warpage to some degree. Accordingly, pursuant to a further feature of the present invention, compensation for the above-mentioned surface attitude changes may be effected by providing a clamping arrangement whereby a central portion of the disc may be clamped to a turntable while the outer circumference bead of the disc is clamped between a roller bearing and a low friction finger (e.g., of nylon) to reduce warpage along the scanned radius.

In accordance with another aspect of the present invention relative motion between the grooved surface and the probing beam is established in such a manner that a succession of regions of the grooved surface are scanned by the probing beam in a radial pattern. Illustratively, the desired relative motion is established by rotating the disc at a first selected rate, while successively translating the beam in a radial direction, while respect to the disc, at a second selected rate. Through choice of the rates, the coarseness of the radial scanning pattern may be controlled whereby the entire grooved surface of the disc may be scanned for defect detection purposes in one revolution of the disc and in a time period which is short (e.g., 3 seconds) relative to the normal playing time (e.g., 30 minutes) of the disc surface.

Pursuant to a further feature of the present invention, the translation of the probing beam along a radius of the inspected disc, is readily accomplished by means of a rotating polygon having mirrors forming its sides. With the center of the polygon at the second focal point of a third lens, whose focal length greatly exceeds the diameter of the polygon, the light beam reflected off the polygon sides and passing through the lens will approximate a beam source at the focal point of the third lens. Angular translation of the probing beam, as the mirror is rotated will approximate at the other side of the lens as a linear translation of the probing beam. This beam translating method enables the Fourier transformation of the light amplitude data of the reflected beams to be immobilized at the focal plane of the first lens so that blocking means, when positioned in that focal plane can be designed to intercept a reduced amount of reflected light, which still includes the diffraction order cones of light, thereby enhancing system sensitivity.

Pursuant to yet another aspect of the present invention, a defect recording apparatus is comprised within the system of the present invention. High speed writing apparatus, for mapping 1:1 polar plots of grooved disc defect locations on disc-shaped photosensitive paper, accepts electrical signals representing defect occurrences. These signals activate an optical modulator that permits passage of a recording beam of light between a light source and a surface of a turntable, upon which the photosensitive paper is mounted. By locating the recording light parallel to and in close proximity to the probing beam, the rotating mirror effects deflection of the recording beam in a manner causing it to scan the paper disc surface in a radial scanning pattern in synchronization with the probing beam scanning of the grooved disc. Moreover, by rotating the paper supporting and the grooved disc supporting turntables in synchronism, markings resulting from modulator activations are caused to be located on the photosensitive paper with radial and circumferential positions corresponding to the locations of the defects appearing on the grooved disc.

Pursuant to a further feature of the present invention, where dust particles exist on the surface of the disc record, care must be taken to minimize the light scattering effect thereof, which produces, at the photodetector, erroneous indications of groove defects. To this end, means, such as a fiber optic probe, are provided to collect the wide angle scattered light reflected by dust particles. Dust detector means responsive to the collected wide angle scattered light provides signal effective, when combined with the output of the photodetector, in reducing the mistaken identification of dust as defects.

In the accompanying drawings:

FIG. 2 illustrates a portion of the defect detection system of FIG. 1, relating to the processing of the reflected light diffraction orders; and FIG. 3 provides a plan view of a defect location record formed by the FIG. 1 system.

Figure 1:
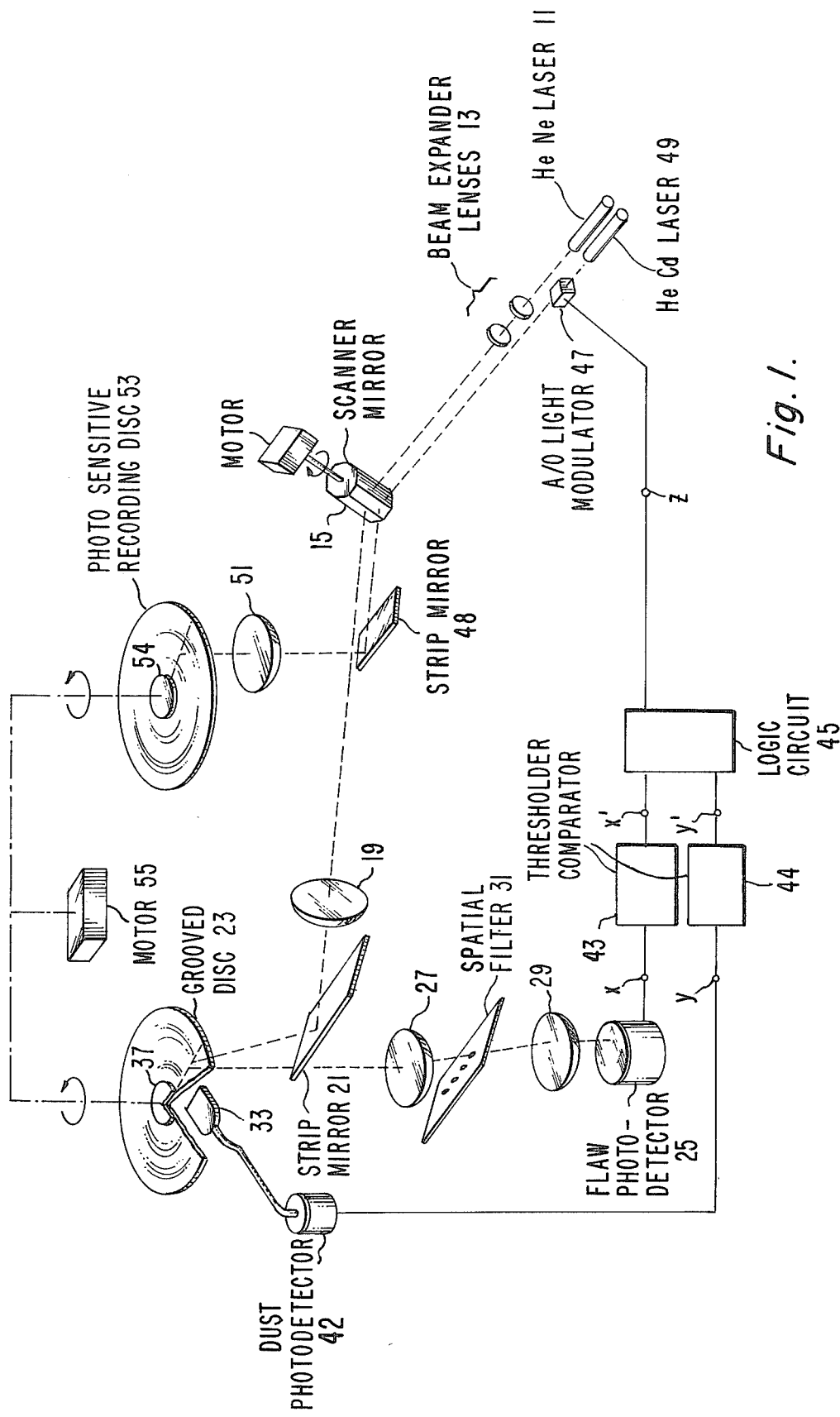
FIG. 1 illustrates, in a perspective view, a grooved disc defect detection and plotting system embodying the principles of the present invention.

Referring to FIG. 1, a coherent light beam from a light source 11 (illustratively, in the form of a HeNe laser), transmitted by a pair of beam expander lenses 13, is intercepted by the reflected surface of a scanner mirror 15 (e.g., pentagonal cylinder). The beam impinging upon the scanner mirror 15 is reflected thereby towards a lens 19 which focuses the light beam toward a point beyond the reflecting surface of a strip mirror 21. The converging beam impinging upon the strip mirror 21 surface is reflected thereby toward the surface of a rotating grooved disc 23 and converges toward a focus point near the surface of record 23, forming a light spot at the intercepting surface region of such a size that a plurality of convolutions of the record's spiral groove (e.g., 30 convolutions of a 5,555 convolution inch disc record) are illuminated.

The orientation of the incident beam is desirably such that the axis of the incident beam lies in a nonparallel relationship, and at a chosen angle (e.g., 2°) with respect to the central axis of the record, and is desirably positioned in a plane which is parallel to said central axis and which intersects the grooved surface along a tangent to a groove convolution at the point of incidence.

Scanning of the surface of the grooved disc 23 is accomplished by rotating the disc 23 while radially translating the incident beam by rotating scanner mirror 15 (e.g., at 3600 rpm). By choosing a radius for the scanner mirror which is small relative to the focal length of focusing lens 19 and by locating the scanner mirror at the focal point of that lens, a so-called flat field scan translation of the probing beam with respect to the surface of a grooved disc 23 is effected, causing the illuminating light spot to scan the record surface in a radial pattern.

Light is reflected by the illuminated grooved surface region towards a first photodetector 25 through a second and third lenses 27, 29 and a blocking means (spacial filter 31) interposed between these two lenses. Portions of the wide angle light reflected by dust in the illuminated disc surface region is collected by means of a fiber optic collector 33 and directed towards a second photodetector 35.

The groove structure in the illuminated region, in the absence of defects and dust particles, provides a regular pattern of depressions and elevations, which effectively serves as a diffraction grating (with a grating pitch determined by the groove convolution pitch) to diffract the light passing to the first photodetector in a fixed pattern. This light diffraction results in the formation of an undeviated zero diffraction order cone of light and a plurality of additional, deviated cones of light corresponding to higher diffraction orders.

As shown in FIG. 2, an undeviated zero diffraction order cone ($d_o$) and a plus and minus first diffraction order cones ($d+1$ and $d-1$) converge at respective points beyond the second lens 27.

Second lens 27 provides a Fourier transformation, in the focal plane thereof, of the light amplitude data of the diffraction order cones. As the light spot radially scans the surface of the disc record 23, the accompanying radial displacement of the diffraction order cones of light across the face of the second lens 27 is accomplished in a manner which maintains the respective angles between the diffraction order cones of light and the lens axis constant (due to the aforementioned flat field scan translation of the incident beam). Therefore, each diffraction order cone of light as it passes the lens 27 is brought to a stationary focus in the focal plane of the second lens 27. Spatial filter 31 is provided with a plurality of light blocking means ($B_1$, $B_2$, etc.), each of which being disposed at a respective focus point, in the focal plane of lens 27, of the diffraction order cones of light to intercept the same. However, when defects disturb the regularity of the groove structure in an illuminated region, confinement of light to the aforesaid cones is no longer maintained, and the unblocked regions of the spacial filter 31 will transmit light energy to photodetector 25, which is converted thereby to electrical energy signalizing the illumination of a defect in the spiral grooves.

An arrangement, useful in compensating for the disc warp when a less than rigid groove disc is being inspected, includes a turntable 37 with a center post clamp which cooperates with a roller bearing 41 to position the outer perimeter of grooved disc 23 by pushing it slightly toward an optic fiber collector 33. The deflection of the perimeter of the disc by the roller bearing may be compared to that affecting a floppy disc whereby any sag or warp in the disc is removed along that radius which includes the roller bearing 41, and along which the illuminating spot is translated. For badly warped discs a low friction button 39 is used to oppose the roller bearing 41 and prevent contact of the disc with the optic fiber collector 33. This arrangement provides reasonable assurance that the disc record surface will be flat and will maintain a constant attitude relative to the incident beam.

With reference again to FIG. 1, the output of photodetector 25, developed at terminal X is indicative of the illumination of a defect in the spiral grooves. However, where dust particles exist on the surfaces of the groove, care must be taken to minimize the light scattering effect thereof, which produces at the photodetector 25, erroneous indications of groove defects. To reduce the effect of said erroneous indications, portions of the wide angle light reflected by dust particles in the illuminated grooved surface region is collected by means of the optic fiber collector 33 and directed towards a second photodetector 42.

The electrical output of first photodetector 25 signalling the illumination of a defect, appears at terminal X as a DC voltage which varies in amplitude in proportion with the amount of light energy that is converted to electrical energy by photodetector 25 (i.e., low levels of illumination produce low amplitude voltages, while high levels of illumination produces high amplitude voltages.)

Similarly, the electrical output of photodetector 42 signalling the illumination of dust particles appears at terminal Y as a DC voltage which varies in amplitude in proportion with the amount of light energy that is converted to electrical energy by photodetector 42 (i.e., low levels of illumination produce low amplitude voltages, while high levels of illumination produces high amplitude voltages).

The outputs of photodetectors 25 and 42 are applied to corresponding threshold circuits 43, 44. Threshold circuits 43, 44 generate voltage outputs at respective terminals x', y' when the input signal to the respective threshold circuit exceeds a respective reference value. A logic circuit 45 produces an output only upon signal development at terminal x' in the absence of signal development at terminal y'. In this manner, reasonable assurance can be provided that only defect signals are recorded. While a small percentage of groove defects will not be recorded due to their scattering light into the fiber optic collector 33, and a small percentage of dust particles will produce defect indication signals due to their peculiar light scattering pattern, overall system sensitivity to dust particles is reduced and system sensitivity to groove defects is enhanced.

The output of the logic circuit 45 which appears at terminal Z is coupled to an acousto-optic light modulator 47 interposed in the path of a recording light beam from a source 49 (e.g., in the form of a He Cd laser). The light output of modulator 47 varies between a high intensity level, during the presence of an output at terminal Z, and a low intensity level in the absence of an output at terminal Z.

The recording light beam, after passing through modulator 47 is intercepted by the reflecting surface of the scanner mirror 15, which effects a translation of the recording beam in synchronism with the translation of the probing beam and which recording beam is reflected thereby towards a strip mirror 48. Mirror 48 reflects the recording beam towards a lens 51 which focuses the recording light beam toward a point on the surface of a photosensitive recording disc 53 (e.g., a disc cut from a sheet of Kodak Linagraph direct print paper, Type 2167), which is sensitive only to the high intensity level output of modulator 47.

Photosensitive disc 53 is supported on a turntable 54 which is rotated in synchronism with the rotation of turntable 37, so that the recording beam traces a radial path on photosensitive disc 53 that substantially matches the radial path traced by the probing beam over the grooves of the disc record 23. Time delay in the acousto-optic modulator 47 is readily compensated for by appropriate tilting of mirror 48. An illustrative arrangement for effecting the desired synchronization is shown in FIG. 1, where both the grooved disc 23 and the photosensitive paper 53 are driven by one motor 55 with the same gearing ratio linkage to turntables 37, 54 supporting the respective discs.

In reference to FIG. 3, an illustrative example of a 1:1 polar plot of defect locations on photosensitive paper 53 is developed by the apparatus of FIG. 1, is presented. The defect locations are represented by each of the dash markings on the plot. The marking A points out the location of one of the several locations occurring near the outer perimeter of the disc record.

I claim:

1. A flaw detection system for detecting defects in a spiral groove formed in a surface of a disc, said system comprising:

means for illuminating a region of the grooved surface of said disc, the illuminated region being sufficiently large to span a plurality of convolutions of said spiral groove;

said illuminating means including means for forming a beam of light directed toward said surface along an incident beam path, and converging toward a point near said surface; the orientation of the axis of said path being normally such that said axis lies in non-parallel relationship, and at a chosen angle, with respect to the central axis of said disc in a first plane normal to the disc surface which intersects a tangent to a groove convolution;

the structure of the groove convolutions in the surface region illuminated by said light beam, absent any defects, serving as a diffraction grating for diffracting light reflected from said illuminated region to form an undeviated zero diffraction order cone converging at a first location in a second plane spaced from the grooved surface of said disc and deviated higher diffraction order cones of light respectively converging at additional locations in said second plane separated from said first location;

means for establishing relative motion between said grooved surface and said beam path in such a manner that said light beam scans a succession of radially aligned regions of said grooved surface;

light detection means having a photosensitive surface;

a light path optically coupling said illuminated regions and said photosensitive surface;

means acting on diffracted order cones of light reflected within said light path from the illuminated regions for substantially replicating the image of said illuminated region at the surface of said light detection means;

light blocking means positioned in said light path for intercepting diffraction order cones of light reflected within said light path;

means responsive to signals developed by said light detection means for indicating illumination of a defect;

a turntable having a flat surface upon which a photosensitive paper is subject to reception;

means for generating a recording beam for effecting an inscription of marks on the photosensitive paper;

a recording beam path optically coupling said beam generating means and said turntable;

means for establishing relative motion between said turntable and said recording beam path in a manner causing said recording beam to scan said turntable along a path in synchronism with the scanning of the grooved surface of said disc by said incident illuminating beam path;

selectively actuated means for varying the intensity of said recording beam between a high intensity level sufficient to effect an inscription of marks on the photosensitive paper and a low intensity level insufficient to effect an inscription of marks on the photosensitive paper; and means for actuating said selectively actuated means in response to the output of said indicating means.

2. A flaw detection system for detecting defects in a regularly grooved surface, said system comprising:

means for illuminating a region of the grooved surface, the illuminated region being sufficiently large to span a plurality of groove segments;

said illuminating means including means for forming a beam of light directed toward said surface along an incident beam path, and converging toward a point near said surface;

the structure of the regularly grooved surface region illuminated by said light beam, absent any defects, serving as a diffraction grating for diffracting light reflected from said illuminated region to form respectively separated diffraction order cones of light;

means for establishing relative motion between said beam path and said grooved surface in a manner causing said incident beam to be translated along the grooved surface while said grooved surface is rotated about a stationary axis;

light detection means having a photosensitive surface;

means for capturing a portion of light reflected from the illuminated region, said capturing means includes means for spatially immobilizing the diffraction order cones of light contained in the captured light;

means for replicating, from the captured light, an image of the illuminated region at the photosensitive surface;

means for preventing diffraction order cones of light contained in the captured light from reaching the photosensitive surface;

means responsive to signals developed by said light detection means for indicating illumination of a defect;

additional light detection means having a photosensitive surface;

a light path optically coupling light reflected at small angles to the disc surface by said illuminated regions with the surface of said additional light detection means; and means, responsive to the output of said additional light detection means, for effecting a reduction of erroneous indications of defects from said indicating means.

3. A flaw detection system for detecting defects in a grooved surface of a disc, said system comprising:

means for illuminating a region of the grooved surface of said disc, the illuminated region being sufficiently large to span a plurality of groove convolutions of said grooved surface;

the structure of the groove convolutions in the surface region illuminated serving as a diffraction grating for diffracting light reflected from said illuminated region to form an undeviated zero diffraction order cone and deviated higher diffraction order cones of light;

first light detection means having a photosensitive surface;

a first light path optically coupling said illuminated region and said photosensitive surface;

light blocking means positioned in said first light path for intercepting diffraction order cones of light reflected within said first light path when a defect free surface region is illuminated;

means responsive to signals developed by said first light detection means for indicating illumination of a defect;

second light detection means having a photosensitive surface;

a second light path optically coupling light reflected, at small angles to the disc surface, by said illuminated regions with the surface of said second light detection means, and means, responsive to the output of said second light detection means, for effecting a reduction of erroneous indications of defects from said indicating means.

4. Apparatus in accordance with claim 3 further comprising:

means for rotating said grooved disc; and wherein said illuminating means includes means for effecting illumination of the disc surface in a manner providing successive illumination of radially aligned regions of the disc surface.

5. Apparatus in accordance with claim 4 wherein said illumination effecting means comprises:

a lens;

a polygonal cylinder mirror, having a diameter which is small relative to the focal length of said lens; said cylinder mirror being positioned such that the center thereof substantially coincides with the second focal point of said lens; and means for rotating said cylinder mirror.

* * * * *